US005888795A

United States Patent [19]
Hamilton

[11] Patent Number: 5,888,795
[45] Date of Patent: Mar. 30, 1999

[54] THERMOSTABLE URACIL DNA GLYCOSYLASE AND METHODS OF USE

[75] Inventor: Paul T. Hamilton, Cary, N.C.

[73] Assignee: Becton, Dickinson and Company, Franklin Lakes, N.J.

[21] Appl. No.: 926,055

[22] Filed: Sep. 9, 1997

[51] Int. Cl.$^6$ .............................. C12N 9/24; C12N 15/56
[52] U.S. Cl. ................ 435/200; 435/320.1; 435/252.33; 435/476; 435/488; 536/23.2
[58] Field of Search .................................. 435/200, 320.1, 435/252.33, 476, 488; 536/23.2

[56] References Cited

PUBLICATIONS

P. Glaser, et al. "Bacillus subtilis genome project: cloning and sequencing of the 97 kb region from 325° to 333°" *Molec. Microbiol.* 10:371–384 (1993).

O. K. Kaboev, et al. "Uracil–DNA Glycosylase From *Bacillus stearothermophilus*" *FEBS Lett.* 132:337–340 (1981).

A. Koulis, et al. "Uracil–DNA glycosylase activities in hyperthermophilic micro–organisms" *FEMS Microbiol. Lett.* 143:267–271 (1996).

M. C. Longo, et al. "Use of uracil DNA glycosylase to control carry–over contamination in polymerase chain reactions" *Gene* 93:125–128 (1990).

U. Varshney, et al. "Sequence Analysis, Expression, and Conservation of *Escherichia coli* Uracil DNA Glycosylase and Its Gene (ung)" *J. Biol. Chem.* 263:7776–7784 (1988).

O. K. Kaboev, et al. "Uracil–DNA Glycosylase of Thermophilic Thermothrix thiopara" *J. Bacteriol.* 164:421–424 (1985).

R. D. Fleischmann, et al. "Whole–Genome Random Sequencing and Assembly of *Haemophilus influenzae* Rd" *Science* 269:496–512 (1995).

V. Mejean, et al. "Nucleotide sequence of the *Streptococcus pneumoniae* ung gene encoding uracil–DNA glycosylase" *Nucl. Acids Res.* 18:6693 (1990).

UCL Protein Crystallography Group "Uracil–DNA Glycosylase". http://bsmcha 1.biochem.ucl.ac.uk/bsm/xtal/udgase.html.

NCBI Complete Genomes (*Haemophilus influenzae*). www.ncbi.nim.nih.gov/cgi–bin/Complete Genomes/prot?HIN1155.

*Primary Examiner*—Charles L. Patterson, Jr.
*Attorney, Agent, or Firm*—Donna R. Fugit

[57] ABSTRACT

A novel uracil DNA glycosylase enzyme (referred to as Bpa UDG) has been identified in *Bacillus pallidus* and the gene encoding Bpa UDG has been cloned, sequenced and expressed to produce a recombinant UDG protein. The enzyme is thermostable and exhibits reaction kinetics similar to *E. coli* UDG. It is effectively inhibited by *B. subtilis* UGI.

Bpa UDG may be used to inactivate contaminating amplicons in nucleic acid amplification reactions, particularly at higher reaction temperatures. It may also be used to generate Bpa UDG-specific antibodies for purification of Bpa-UDG or for detecting Bpa UDG in a sample. Certain Bpa UDG antibodies may inactivate the enzyme and may therefore be useful as substitutes for UGI or heat, or in combination with UGI and/or heat, for controlling UDG activity in a reaction.

20 Claims, No Drawings

THERMOSTABLE URACIL DNA GLYCOSYLASE AND METHODS OF USE

FIELD OF THE INVENTION

The invention relates to uracil DNA glycosylase enzymes, genes coding for uracil DNA glycosylase and use of uracil DNA glycosylase in biochemical reactions. Also provided are antibodies which recognize and bind to uracil DNA glycosylase and methods of using these antibodies.

BACKGROUND OF THE INVENTION

Uracil is a normally-occurring base in RNA. However, uracil may also be found in DNA due to deamination of cytosine or misincorporation of dUTP during DNA replication. Because uracil will base-pair with adenine, deamination of cytosine results in a transition mutation from G:C to A:T. All known DNA-containing organisms therefore have a specific repair mechanism for removing uracil from DNA. The enzyme uracil DNA glycosylase (UDG) catalyzes the first step of the repair pathway, in which the N-glycosidic bond between uracil and the deoxyribose sugar is hydrolyzed. Other enzymes then repair the abasic site. UDG may also be referred to as uracil N-glycosylase (UNG). The UDG enzyme is highly specific for removal of uracil in DNA. It does not have any detectable excision activity against uracil in RNA (which could potentially inactivate mRNA, rRNA and tRNA in the cell) nor does it have any detectable activity against thymine in DNA (which would compromise the structure and stability of chromosomal DNA).

The UDG enzyme of the mesophilic organism *Escherichia coli* has been studied the most extensively, and the gene encoding the protein (ung) has been cloned (U. Varshney, et al. 1988. *J. Biol. Chem.* 263:7776–7784). The UDG genes of herpes simplex virus type-1, *Haemophilus influenzae* (1995. *Science* 269(5223):496–512), *Streptococcus pneumoniae* (1990. *Nucl. Acids Res.* 18(22):6693) and *Bacillus subtilis* (1993. *Mol. Microbiol.* 10(2):371–384) have also been isolated and sequenced. Thermophilic UDG proteins have been isolated from the thermophilic bacteria *Bacillus stearothermophilus* and *Thermothrix thiopara*, which have optimum temperatures for growth of 55° C. and 75° C., respectively (O. K. Kaboev, et al. 1981. *FEBS Lett.* 132:337–340; O. K. Kaboev, et al. 1985. *J. Bacteriol.* 164:421–424). The UDG genes are fairly homologous. However, in spite of sequence divergence demonstrated by hybridization studies and sequence analysis, the tertiary structure of the UDG enzymes has been found to be highly conserved (U. Varshney, et al., supra).

Nucleic acid amplification reactions are processes by which specific nucleic acid target sequences are amplified. Amplification methods have become powerful tools in nucleic acid analysis and preparation and several nucleic acid amplification methods are known. These include the Polymerase Chain Reaction (PCR), Self-Sustained Sequence replication (3SR), Nucleic Acid Based Sequence Replication (NASBA), the Ligase Chain Reaction (LCR), Qβ replicase amplification and Strand Displacement Amplification (SDA). Unfortunately, the powerful ability of these nucleic acid amplification methods to amplify minute quantities of a target sequence also make them susceptible to contamination by copies of target sequences (amplicons) which may be carried over from previous amplification reactions in reagents, pipetting devices and laboratory surfaces. These contaminating products of previous amplifications may themselves be amplified in a subsequent amplification reaction. Even a few molecules of a contaminating target sequence may be readily amplified and detected, resulting in falsely positive results.

Recently developed methods for inactivating contaminating amplicons in nucleic acid amplification reactions such as PCR and SDA involve incorporation of the nucleotide deoxyuridine triphosphate (dUTP) into amplified nucleic acid sequences in place of thymidine triphosphate (TTP). As deoxyuridine (dU) is rarely found in naturally-occurring DNA, this nucleotide serves to distinguish previously produced amplicons from new target sequences which have not yet been amplified. The uracil-containing DNAs, representing previously amplified contaminating sequences, are treated with UDG to remove the intentionally incorporated uracil in amplified nucleic acid. Uracil is removed without destruction of the sugar-phosphodiester backbone, thereby producing an abasic site in the DNA. These abasic sites are susceptible to hydrolysis by heat or alkali, a process which fragments the uracil-containing DNA and renders it unamplifiable in a subsequent nucleic acid amplification reaction. UDG is inactivated prior to beginning the subsequent amplification reaction to prevent removal of uracil residues from newly generated amplicons. Fragmentation of the nucleic acids is optional, as it has been found that the abasic sites alone are sufficient to prevent amplification.

As *E. coli* UDG has been the preferred enzyme for decontamination of nucleic acid amplification reactions, it is typically inactivated by incubation at high temperatures (70°–80° C.). In fact, mesophilic UDG's are substantially inactive at the elevated temperatures used for PCR amplification reactions. However, it has been shown that upon return of the PCR sample to 4°–25° C. after amplification, sufficient UDG activity is still present to degrade dU-PCR amplification products. It has therefore been recommended that PCR reactions be maintained at elevated temperatures after UDG treatment (Rashtchian, A., Hartley, J. L. and Thornton, C. G., *Biotechniques*, volume 13, No. 2, page 180). To address the problem of residual UDG activity after heat inactivation, WO 92/01814 describes a thermolabile UDG enzyme.

The *Bacillus subtilis* bacteriophage PBS1 is unique in that it uses uracil instead of thymine in its DNA. This phage must therefore protect itself from host cell UDG's upon infection. To do so, PBS1 produces a uracil glycosylase inhibitor protein (UGI) which complexes with UDG's and inactivates them. The PBS1 gene encoding UGI, and genes from closely related *B. subtilis* PBS phages such as PBS2, have been cloned and expressed to produce recombinant UGI. The UGI protein has been shown to be an effective means for controlling residual UDG activity still present after heat inactivation in PCR (Rashtchian, et al., supra). It has further been shown that UGI alone is effective to inactivate UDG in isothermal amplification reactions such as Strand Displacement Amplification (SDA), which do not have high temperature cycling and which may be incompatible with high temperature steps for inactivation of UDG.

As previously stated, genes coding for mesophilic UDG's have been cloned and expressed to produce recombinant UDG's for use in decontamination of nucleic acid amplification reactions. However, temperature cycling amplification reactions such as PCR are typically performed at thermophilic temperatures and it is advantageous to perform isothermal amplification reactions such as SDA at thermophilic temperatures to improve the speed and specificity of the reaction. Such thermophilic amplification reactions would benefit from the availability of a thermostable UDG which would be active at the preferred temperature of the amplification reaction. Such a thermophilic UDG would permit the practitioner to perform decontamination at a higher temperature which may be similar to or the same as the thermophilic amplification reaction (e.g., 45°–75° C.). This makes the steps of the process more efficient, as the magnitude of the temperature changes required to decontaminate the sample, increase temperature to inactivate the UDG, and re-equilibrate the sample to the reaction temperature is significantly reduced as compared to decontamination at mesophilic temperatures (e.g., 35°–45° C.).

SUMMARY OF THE INVENTION

A novel UDG enzyme, referred to as Bpa UDG, has been identified in Bacillus pallidus. The gene encoding this UDG has been cloned, sequenced and expressed to produce a recombinant Bpa UDG protein. The enzyme is thermostable, consistent with its isolation from a thermophilic organism, and exhibits reaction kinetics similar to E. coli UDG. It is effectively inhibited by B. subtilis UGI.

Bpa UDG may be used to inactivate contaminating amplicons in nucleic acid amplification reactions, particularly at reaction temperatures in the thermophilic range (about 45°–75° C.). It may also be used to generate Bpa UDG-specific antibodies for purification of Bpa-UDG or for detecting Bpa UDG in a sample. Certain Bpa UDG antibodies may inactivate the enzyme and may therefore be useful as substitutes for UGI and heat, or as a complement to UGI and heat, for controlling UDG activity in a reaction.

DETAILED DESCRIPTION OF THE INVENTION

To clone the UDG gene from Bacillus pallidus, the known amino acid sequences of UDG from E. coli, H. influenzae, B. subtilis and S. pneumoniae were aligned to identify conserved regions. Conserved sequences GQDPYHGP (SEQ ID NO:1, corresponding to residues 62–29 of the E. coli sequence) and WAKQGVLL (SEQ ID NO:2, corresponding to residues 114–121 of the E. coli sequence) were selected as the basis for design of PCR primers which were synthesized using preferred codons in B. pallidus:

GGACAAGATCCGTATCATGGACC ("BPAUNG-F", SEQ ID NO:3)

CAAAAGAACTCCTTGTTTTGCCCA ("BPAUNG-R", SEQ ID NO:4)

Preferred B. pallidus codon useage had been previously determined in connection with cloning of a DNA polymerase gene from that organism.

SEQ ID NO:3 and SEQ ID NO:4 were used as forward and reverse primers in PCR amplification reactions using genomic DNA from B. stearothermophilus, Saccharrococcus thermophilus (Sth), and B. pallidus (Bpa) as templates. Amplification products were obtained from B. pallidus (180 base pairs) and S. thermophilus but not from B. stearothermophilus. The PCR amplification products of Bpa and Sth were sequenced and aligned with known gene sequences for E. coli, B. subtilis, Streptococcus pneumoniae and H. influenzae to evaluate the extent of homology. Significant homology was found (50–70% identity with the four other UDG gene sequences), indicating a high likelihood that the Bpa and Sth PCR amplification products were fragments of their UDG genes.

To isolate the full-length genomic copy of the Bpa UDG gene, a genomic library of B. pallidus DNA was constructed by cloning genomic DNA digested with BclI into a λZAP vector (Stratagene). The Bpa UDG PCR product was radio-labelled and used to screen the library by hybridization. Four clones which were positive by hybridization were selected for further characterization by restriction mapping and re-amplification using SEQ ID NO:3 and SEQ ID NO:4. One of the four clones (#3-2) contained an approximately 4.1 Kb insert and was selected for sequencing of the region between the PCR primers. The #3-2 clone was found to contain the full-length coding sequence for Bpa UDG as well as three other potential open reading frames downstream from the Bpa UDG gene. The coding sequence of the full-length Bpa UDG gene is shown in SEQ ID NO:5 and the deduced amino acid sequence of the Bpa UDG encoded by SEQ ID NO:5 is shown in SEQ ID NO:6.

The coding sequence of the UDG gene was subcloned into expression plasmid pTRC99A (Pharmacia) as follows. A PCR primer containing an NcoI cloning site and a PCR primer containing a BamHI cloning site were used to amplify the coding region of the Bpa UDG gene (GGCAAACCATGGAGCAGATTTTAAAAAATGATTGG, SEQ ID NO:7; GTTTCTGGATCCGTTGGATTTATGGATAGTCCCT, SEQ ID NO:8, respectively). The appended restriction sites were used to clone the coding region in the pTRC99A plasmid. The inserts of several clones were characterized and found to contain fragments of the predicted size for the full length coding sequence of the Bpa UDG gene. They also produced an approximately 27 Kd protein upon induction with IPTG, consistent with expression of Bpa UDG. One of these clones, designated pTRC/UNG-1, was deposited under the Budapest Treaty with the American Type Culture Collection, Rockville, Md., as ATCC Accession No. 98514 on Aug. 22, 1997. The recombinant Bpa UDG was isolated by size exclusion chromatography (e.g., SUPERDEX) from lysates of induced host cells as described below and further characterized. The protein exhibited similar kinetics to E. coli UDG and was inhibited by phage UGI protein. In contrast to the E. coli enzyme, however, it was fully active at 60° C., consistent with its isolation from a thermophilic organism. It is estimated that the Bpa UDG enzyme is active between about 45° C. and 75° C.

Fusion of the Bpa UDG protein to heterologous amino acid sequences (i.e., amino acid sequences not found in the naturally occurring Bpa UDG protein) provides alternative methods for isolation or purification of recombinant Bpa UDG. For example, the coding sequence may be cloned into the pMAL-c plasmid (New England BioLabs), placing the coding sequence of the gene under the control of the lac promoter of E. coli. Upon induction with IPTG, transformed host cells express a fusion protein comprising the protein to be expressed fused to the maltose binding protein (MBP, the malE gene product). The MBP portion of the fusion protein allows purification of the expression product on amylose resin as is known in the art. The MBP affinity tag may be at either the C-terminus or the N-terminus of the fusion protein. Alternatively, a nucleotide sequence coding for consecutive histidine residues at the C-terminus or the N-terminus of Bpa UDG may be inserted in the expression vector. Polyhistidine is useful for purification of proteins by immobilized metal affinity chromatography ("MAC", e.g., by binding to nickel) using methods known in the art. Because they facilitate purification of proteins by specific binding to a ligand, MBP, polyhistidine and other similar heterologous sequences are referred to as "affinity purification tags."

The heterologous sequence fused to the Bpa UDG protein may also be an N-terminal secretory signal sequence which provides transport of recombinant Bpa UDG into the cell culture medium. Methods for cloning a sequence to be expressed adjacent to a heterologous signal sequence to obtain secretion of the recombinant protein are also well known in the art. Upon culture of the transformed host cell and expression of the recombinant protein, the recombinant protein is transported out of the cell into the culture medium by means of the secretory signal sequence. The Bpa UDG may then be isolated or purified from the culture medium without the need to lyse the host cells.

When no affinity purification tag is present the UDG protein may be isolated or purified using standard methods. For example, *E. coli* cells expressing recombinant Bpa UDG may be isolated from the culture medium, resuspended in a lysis buffer (e.g., 30 mM TRIS-HCl pH 7.4, 65 mM NaCl, 5% glycerol (w/v), 1 mM EDTA, 1 mM DTT), sonicated to lyse the cells and centrifuged to remove cell debris. Of course, lysis of the cells is not necessary when a secretory expression system for the recombinant UDG is employed. In secretory expression systems the cells are separated from the culture medium and the culture medium rather than a cell lysate is processed to isolate the UDG. The supernatant of the centrifuged cell lysate is then typically heated at 65° C. for 10 min. in a water bath and centrifuged to denature and pellet temperature-sensitive contaminating proteins. The Bpa UDG may then be fractionated from the supernatant by size exclusion chromatography (e.g., on SUPERDEX 200, Pharmacia), collecting fractions and assaying them for enzymatic activity. Active fractions are typically pooled and on ethidium bromide stained agarose gels show no detectable nucleic acid contamination. On Coomassie blue stained SDS PAGE gels, the pooled active fractions of SUPERDEX 200 chromatography appear as a single band, indicating a relatively high degree of purity. Other suitable conventional purification methods will be apparent to those skilled in the art without the exercise of inventive skill, for example, ammonium sulfate fractionation and a variety of chromatography methods (including but not limited to affinity chromatography). Such purification procedures may also be applied for isolation or purification of the naturally-occurring (i.e., nonrecombinant) Bpa UDG protein from the *B. pallidus* microorganism. The isolated or purified naturally occurring Bpa UDG enzyme is expected to exhibit the same sequence characteristics as the recombinant, as well as similar properties and utilities, and may be substituted for recombinant Bpa UDG in the methods described herein.

Due to the known degeneracy of the genetic code, it will be apparent to one skilled in the art that different but equivalent nucleotide sequences which code for the Bpa UDG enzyme of the invention (e.g., as shown in SEQ ID NO:6) may be isolated, synthesized or otherwise prepared without the exercise of inventive skill. Such degenerate coding sequences are included within the scope of the invention. It is also within the ordinary skill in the art to clone DNA fragments encoding the Bpa UDG of the invention into a variety of cloning vectors and to express the recombinant Bpa UDG protein under the control of a selected promoter in a variety of transformed prokaryotic and eukaryotic host cells.

Monoclonal and polyclonal antibodies which recognize and bind to Bpa UDG may be prepared using the Bpa UDG of the invention. Polyclonal antibodies are generally produced by immunizing animals with an enriched or purified preparation of Bpa UDG according to conventional protocols. The preferred antigen for immunization is a preparation of isolated or purified Bpa UDG, but crude extracts may also be used. Isolated recombinant Bpa UDG is the preferred antigen for immunization. The serum of animals thus immunized contains the polyclonal anti-Bpa UDG antibodies, and the immune serum is often used directly in immunoassays. In this case, the anti-Bpa UDG polyclonal antibodies are isolated in serum by separating the serum from red blood cells and other cellular components of blood. Monoclonal antibodies which recognize the Bpa UDG of the invention may be prepared using the methods of Kohler and Milstein (1975. *Nature* 256:495). Mice may be immunized with the Bpa UDG antigen preparation, the spleen cells fused and the resulting hybridomas screened in enzyme-linked immunosorbent assays (ELISAs) or immunoblots for reactivity with the immunogen. Hybridomas secreting antibodies of interest are typically subcloned. The monoclonal antibody may then be produced by culturing the hybridoma in vitro or in ascites in pristane-primed Balb/C mice. It is then typically isolated from the culture medium or ascites by chromatography on Protein A-Sepharose (Sigma Chemical Co., St. Louis, Mo.). Alternatively, Bpa UDG may be coupled to a solid phase and used to purify polyclonal or monoclonal antibodies by affinity chromatography. Using these methods, a variety of hybridomas which produce anti-Bpa UDG monoclonal antibodies may be identified. Monoclonal antibodies are preferred for immunoassays due to their improved specificity and affinity for the antigen to be detected. Anti-Bpa UDG monoclonal antibodies which recognize different epitopes on the protein may also be useful in studies to evaluate protein structure and function. Anti-Bpa UDG antibodies as described above, preferably monoclonal antibodies, may also be coupled to Protein A-Sepharose as is known in the art for use in affinity purification of naturally-occurring or recombinant Bpa UDG.

What is claimed is:

1. An isolated nucleic acid sequence selected from the group consisting of SEQ ID NO:5 and nucleic acid sequences encoding SEQ ID NO:6.

2. A recombinant vector comprising a nucleic acid sequence according to claim 1.

3. The recombinant vector of claim 2 which is an expression vector.

4. The recombinant vector of claim 3 wherein the nucleic acid sequence is linked to a second nucleic acid sequence encoding a heterologous amino acid sequence.

5. The recombinant vector of claim 4 wherein the heterologous amino acid sequence is an affinity purification tag or a secretion signal sequence.

6. A host cell transformed with the recombinant vector of claim 2.

7. The transformed host cell of claim 6 which is an *E. coli* host cell.

8. A host cell transformed with the recombinant vector of claim 3.

9. The host cell of claim 8 which is an *E. coli* host cell.

10. Clone ATCC Accession No. 98514.

11. A method for producing a recombinant uracil DNA glycosylase comprising culturing the transformed host cell of claim 6 in a culture medium under conditions whereby the recombinant uracil DNA glycosylase is expressed by the transformed host cell.

12. The method of claim 11 wherein expression of the recombinant uracil DNA glycosylase is induced during culture.

13. The method of claim 11 further comprising purifying the expressed recombinant uracil DNA glycosylase from a cell lysate or the culture medium.

14. The method of claim 13 wherein the recombinant uracil DNA glycosylase is purified by means of an affinity purification tag.

15. The method of claim 13 wherein the recombinant uracil DNA glycosylase is purified by size exclusion chromatography.

16. A method of making a recombinant vector for expression of a uracil DNA glycosylase in a transformed host cell comprising cloning a nucleic acid sequence selected from the group consisting of SEQ ID NO:5 and nucleic acid sequences encoding SEQ ID NO:6 into an expression vector under control of a promoter such that the uracil DNA glycosylase is expressible in the transformed host cell.

17. The method of claim 16 wherein the nucleic acid sequence is cloned under control of a lac promoter.

18. The method of claim 16 further comprising linking the nucleic acid sequence in the vector to a nucleic acid sequence encoding a heterologous amino acid sequence such that expression of the uracil DNA glycosylase produces a fusion protein.

19. The method of claim 18 wherein the heterologous amino acid sequence is an affinity purification tag or a secretion signal sequence.

20. The method of claim 19 wherein the affinity purification tag is maltose binding protein or polyhistidine.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: Not Relevant ( x i ) SEQUENCE DESCRIPTION: SEQ ID NO:1:

```
            Gly Gln Asp Pro Tyr His Gly Pro
            1               5
```

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS:
        (D) TOPOLOGY: Not Relevant (xi) SEQUENCE DESCRIPTION: SEQ ID NO:2:

```
        Trp Ala Lys Gln Gly Val Leu Leu
        1               5
```

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:3:

```
GGACAAGATC CGTATCATGG ACC                                               23
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

```
CAAAAGAACT CCTTGTTTTG CCCA                                              24
```

(2) INFORMATION FOR SEQ ID NO:5:

(i) SEQUENCE CHARACTERISTICS:
        (A) LENGTH: 681 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..681

(xi) SEQUENCE DESCRIPTION: SEQ ID NO:5:

```
TTG AAG CAG ATT TTA AAA AAT GAT TGG TGG GGA CTG TTG AAA GAA GAG         48
Leu Lys Gln Ile Leu Lys Asn Asp Trp Trp Gly Leu Leu Lys Glu Glu
1               5                   10                  15

TTT GAA AAG CCA TAC TAC AAA GAG CTG CGG GAA TTT TTG AAG CAG GAA         96
Phe Glu Lys Pro Tyr Tyr Lys Glu Leu Arg Glu Phe Leu Lys Gln Glu
                20                  25                  30

TAT GCC CAT CAT ACG ATT TAT CCG GAT ATG TAC GAC ATT TTT AAT GCT        144
Tyr Ala His His Thr Ile Tyr Pro Asp Met Tyr Asp Ile Phe Asn Ala
            35                  40                  45

TTG CAT TAC ACG CCT TAT GAA GAA GTA AAG GTT GTC ATT TTA GGC CAA        192
Leu His Tyr Thr Pro Tyr Glu Glu Val Lys Val Val Ile Leu Gly Gln
        50                  55                  60

GAT CCG TAT CAT GGA CCA AAT CAA GCA CAT GGA TTA AGC TTT TCC GTA        240
Asp Pro Tyr His Gly Pro Asn Gln Ala His Gly Leu Ser Phe Ser Val
65                  70                  75                  80
```

| | | | | | | | | | | | | | | | | |
|---|---|---|---|---|---|---|---|---|---|---|---|---|---|---|---|---|
| AAG | CCG | GGG | ATT | GCT | CAG | CCG | CCG | TCT | CTG | AAA | AAT | ATT | TTC | ATC | GAG | 288 |
| Lys | Pro | Gly | Ile | Ala | Gln | Pro | Pro | Ser | Leu | Lys | Asn | Ile | Phe | Ile | Glu | |
| | | | | 85 | | | | | 90 | | | | | 95 | | |
| CTT | GAG | AAC | GAT | CTC | GGC | TGC | AAG | CCT | CCA | AAC | CAC | GGT | CAT | CTT | GTC | 336 |
| Leu | Glu | Asn | Asp | Leu | Gly | Cys | Lys | Pro | Pro | Asn | His | Gly | His | Leu | Val | |
| | | | 100 | | | | 105 | | | | | 110 | | | | |
| AAA | TGG | GCG | AAG | CAA | GGT | GTT | CTA | TTA | TTG | AAC | ACT | GTG | CTG | ACG | GTA | 384 |
| Lys | Trp | Ala | Lys | Gln | Gly | Val | Leu | Leu | Leu | Asn | Thr | Val | Leu | Thr | Val | |
| | | 115 | | | | | 120 | | | | | 125 | | | | |
| AGG | CAG | GGA | CTA | GCC | AAT | TCT | CAT | AAA | GGA | AAA | GGA | TGG | GAA | CAA | TTT | 432 |
| Arg | Gln | Gly | Leu | Ala | Asn | Ser | His | Lys | Gly | Lys | Gly | Trp | Glu | Gln | Phe | |
| | 130 | | | | | 135 | | | | | 140 | | | | | |
| ACC | GAT | CGA | GTG | ATT | AGC | TGT | TTA | AAC | GAG | CGA | GAG | CGT | CCA | GTC | GTC | 480 |
| Thr | Asp | Arg | Val | Ile | Ser | Cys | Leu | Asn | Glu | Arg | Glu | Arg | Pro | Val | Val | |
| 145 | | | | | 150 | | | | 155 | | | | | 160 | | |
| TTT | ATT | TTA | TGG | GGA | AGG | CAT | GCA | CAG | GCG | AAA | AAA | GAA | ATG | ATT | AAC | 528 |
| Phe | Ile | Leu | Trp | Gly | Arg | His | Ala | Gln | Ala | Lys | Lys | Glu | Met | Ile | Asn | |
| | | | | 165 | | | | 170 | | | | | 175 | | | |
| ATG | ACT | AAG | CAT | TTT | GTC | ATT | GAG | TCG | CCG | CAT | CCA | TCG | CCA | TTT | TCG | 576 |
| Met | Thr | Lys | His | Phe | Val | Ile | Glu | Ser | Pro | His | Pro | Ser | Pro | Phe | Ser | |
| | | | 180 | | | | 185 | | | | | 190 | | | | |
| GCA | AAC | AGA | GGC | TTT | TTT | GGC | AGC | AGG | CCT | TTT | TCT | AAA | GCA | AAT | CAA | 624 |
| Ala | Asn | Arg | Gly | Phe | Phe | Gly | Ser | Arg | Pro | Phe | Ser | Lys | Ala | Asn | Gln | |
| | | 195 | | | | | 200 | | | | | 205 | | | | |
| TTT | TTA | AAG | TCC | ATC | GGA | TCA | GAA | GAA | ATT | GAC | TGG | TGC | ATC | AGC | GAT | 672 |
| Phe | Leu | Lys | Ser | Ile | Gly | Ser | Glu | Glu | Ile | Asp | Trp | Cys | Ile | Ser | Asp | |
| | 210 | | | | | 215 | | | | | 220 | | | | | |
| AAT | GAC | ATT | | | | | | | | | | | | | | 681 |
| Asn | Asp | Ile | | | | | | | | | | | | | | |
| 225 | | | | | | | | | | | | | | | | |

( 2 ) INFORMATION FOR SEQ ID NO:6:

( i ) SEQUENCE CHARACTERISTICS:
        ( A ) LENGTH: 227 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Leu | Lys | Gln | Ile | Leu | Lys | Asn | Asp | Trp | Trp | Gly | Leu | Leu | Lys | Glu | Glu |
| 1 | | | | 5 | | | | | 10 | | | | | 15 | |
| Phe | Glu | Lys | Pro | Tyr | Tyr | Lys | Glu | Leu | Arg | Glu | Phe | Leu | Lys | Gln | Glu |
| | | | 20 | | | | | 25 | | | | | 30 | | |
| Tyr | Ala | His | His | Thr | Ile | Tyr | Pro | Asp | Met | Tyr | Asp | Ile | Phe | Asn | Ala |
| | | 35 | | | | | 40 | | | | | 45 | | | |
| Leu | His | Tyr | Thr | Pro | Tyr | Glu | Glu | Val | Lys | Val | Val | Ile | Leu | Gly | Gln |
| | 50 | | | | | 55 | | | | | 60 | | | | |
| Asp | Pro | Tyr | His | Gly | Pro | Asn | Gln | Ala | His | Gly | Leu | Ser | Phe | Ser | Val |
| 65 | | | | | 70 | | | | | 75 | | | | | 80 |
| Lys | Pro | Gly | Ile | Ala | Gln | Pro | Pro | Ser | Leu | Lys | Asn | Ile | Phe | Ile | Glu |
| | | | | 85 | | | | | 90 | | | | | 95 | |
| Leu | Glu | Asn | Asp | Leu | Gly | Cys | Lys | Pro | Pro | Asn | His | Gly | His | Leu | Val |
| | | | 100 | | | | 105 | | | | | 110 | | | |
| Lys | Trp | Ala | Lys | Gln | Gly | Val | Leu | Leu | Leu | Asn | Thr | Val | Leu | Thr | Val |
| | | 115 | | | | | 120 | | | | | 125 | | | |
| Arg | Gln | Gly | Leu | Ala | Asn | Ser | His | Lys | Gly | Lys | Gly | Trp | Glu | Gln | Phe |
| | 130 | | | | | 135 | | | | | 140 | | | | |
| Thr | Asp | Arg | Val | Ile | Ser | Cys | Leu | Asn | Glu | Arg | Glu | Arg | Pro | Val | Val |

-continued

```
145                 150                 155                 160
Phe Ile Leu Trp Gly Arg His Ala Gln Ala Lys Lys Glu Met Ile Asn
                165                 170                 175
Met Thr Lys His Phe Val Ile Glu Ser Pro His Pro Ser Pro Phe Ser
            180                 185                 190
Ala Asn Arg Gly Phe Phe Gly Ser Arg Pro Phe Ser Lys Ala Asn Gln
        195                 200                 205
Phe Leu Lys Ser Ile Gly Ser Glu Glu Ile Asp Trp Cys Ile Ser Asp
    210                 215                 220
Asn Asp Ile
225
```

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GGCAAACCAT GGAGCAGATT TTAAAAAATG ATTGG        3 5

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GTTTCTGGAT CCGTTGGATT TATGGATAGT CCCT        3 4